United States Patent [19]
Otaka et al.

[11] Patent Number: 6,049,001
[45] Date of Patent: Apr. 11, 2000

[54] FLUORINE-CONTAINING CARBOXYLIC ACID COMPOUNDS, METHODS FOR THEIR PRODUCTION, AND CHEMICAL PROCESSES UTILIZING THE SAME

[75] Inventors: Ken Otaka, Osaka; Noritada Matsuo, Hyogo, both of Japan

[73] Assignee: Sumitomo Chemical Company, Limited, Osaka, Japan

[21] Appl. No.: 09/362,090

[22] Filed: Jul. 28, 1999

[30] Foreign Application Priority Data

Jul. 31, 1998 [JP] Japan .................................. 10-217307

[51] Int. Cl.[7] .................................................... C07C 69/74
[52] U.S. Cl. ........................ 560/124; 560/227; 562/506; 562/603; 562/605
[58] Field of Search .................................... 560/124, 227; 562/603, 605, 506

[56] References Cited

U.S. PATENT DOCUMENTS 4,332,815  6/1982  Engel .
4,985,457  1/1991  Kishino et al. .

FOREIGN PATENT DOCUMENTS 2006835  6/1990  Canada .

*Primary Examiner*—James H. Reamer
*Attorney, Agent, or Firm*—Pillsbury Madison & Sutro LLP

[57] ABSTRACT

Novel fluorine-containing carboxylic acid compounds of formula (II) are provided that can be reacted together with a base to produce industrially useful 3-(2-chloro-2-fluorovinyl)-2,2-dimethyl cyclopropanecarboxylic acid compounds of formula (I). The fluorine-containing containing carboxylic acid compounds of formula (II), if so desired, can be produced by reacting together a carboxylic acid compound of formula (III) and trichlorofluoromethane. In each of the formulas (I), (II), and (III), R is a lower alkyl group or a hydrogen atom.

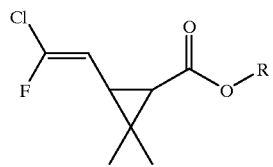

(I)

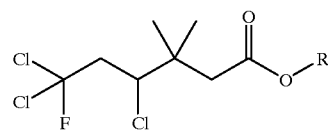

(II)

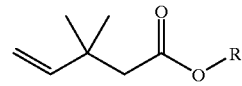

(III)

12 Claims, No Drawings

FLUORINE-CONTAINING CARBOXYLIC ACID COMPOUNDS, METHODS FOR THEIR PRODUCTION, AND CHEMICAL PROCESSES UTILIZING THE SAME

BACKGROUND OF THE INVENTION

1. Field of the Invention

The instant invention relates to fluorine-containing carboxylic acid compounds, methods of producing fluorine-containing carboxylic acid compounds, and methods of producing 3-(2-chloro-2-fluorovinyl)-2,2-dimethylcyclopropanecarboxylic acid compounds using said fluorine-containing carboxylic acid compounds.

2. Description of Related Art

U.S. Pat. No. 4,985,457 discloses certain types of 3-(2-chloro-2-fluorovinyl)-2,2-dimethylcyclopropanecarboxylate ester compounds having pesticidal activity.

Canadian unexamined Patent Publication 2006835 A discloses a method of producing the 3-(2-chloro-2-fluorovinyl)-2,2-dimethylcyclopropanecarboxylic acid portion of said compounds, which is shown in the following formula:

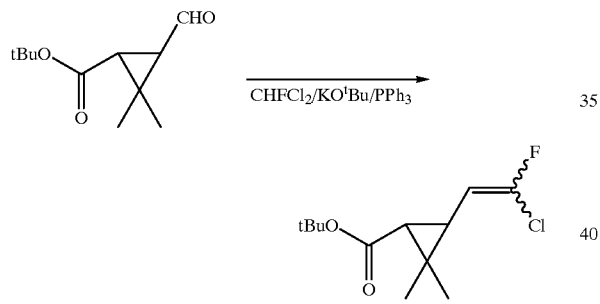

The method of the Canadian Patent fails to be thoroughly advantageous in that said method is not additionally favorable to produce 3-(2-chloro-2-fluorovinyl)-2,2-dimethylcyclopropanecarboxylic acid compounds, such as the ester compounds thereof. In addition, said method of the Canadian Patent fails to be thoroughly advantageous at an industrial scale. For example, the method of the Canadian Patent typically subjects chrysanthemate esters to ozonolysis, in order to produce the starting aldehyde compound of said method. The ozonolysis for the method of the Canadian Patent utilizes the explosive substance of ozone. Further, the method of the Canadian Patent also uses agents which are difficult to industrially manage, such as triphenylphosphine.

SUMMARY OF THE INVENTION

The instant invention provides a method of producing 3-(2-chloro-2-fluorovinyl)-2,2-dimethylcyclopropanecarboxylic acid compounds, which are encompassed by the following formula (I):

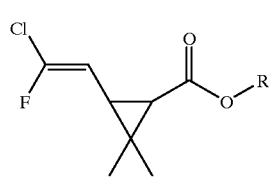

wherein R represents a lower alkyl (e.g., $C_{1-6}$ alkyl) group or a hydrogen atom. Such methods can produce 3-(2-chloro-2-fluorovinyl)-2,2-dimethylcyclopropanecarboxylic acid compounds of formula (I) sufficiently at an industrial scale, while typically averting ozonolysis and agents which are difficult to industrially manage such as triphenylphosphine. In the inventive methods, said 3-(2-chloro-2-fluorovinyl)-2,2-dimethylcyclopropanecarboxylic acids compounds of formula (I) are produced by reacting a base and a fluorine-containing carboxylic acid compound of the instant invention.

Accordingly, the instant invention also provides novel fluorine-containing carboxylic acid compounds, encompassed by the following formula (II):

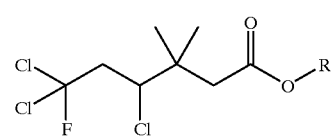

wherein R represents a lower alkyl (e.g., $C_{1-6}$ alkyl) group or a hydrogen atom, and a method of producing said fluorine-containing carboxylic acid compounds of formula (II). Said method of producing said fluorine-containing carboxylic acid compounds of formula (II) comprises the step of reacting a carboxylic acid compound having the following formula (III):

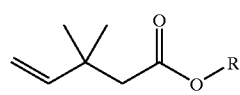

wherein R represents a lower alkyl (e.g., $C_{1-6}$ alkyl) or a hydrogen atom, and trichlorofluoromethane in the presence of at least one metal salt, which is preferably selected from the group consisting of iron halides, copper halides, copper cyanides, and the like.

In addition, the instant invention also provides a method of producing 3-(2-chloro-2-fluorovinyl)-2,2-dimethylcyclopropanecarboxylic acid compounds of formula (I), by reacting a carboxylic acid compound of formula (III) and trichlorofluoromethane as described above to produce a novel fluorine-containing carboxylic acid compound of formula (II) as described above, and thereafter reacting the compound of formula (II) and a base as described above, to give the to give the desired 3-(2-chloro-2-fluorovinyl)-2, 2-dimethylcyclopropanecarboxylic acid compound of formula (I).

DETAILED DESCRIPTION OF THE INVENTION

When referring herein to "acids", such as the fluorine-containing carboxylic acid compounds, carboxylic acid compounds and the like, that term shall broadly be understood to include the free acid or ester compounds of the "acid" or variations of the "acids" which are obvious to those of ordinary skill in the art (e.g. acid salts thereof).

In one aspect, the instant invention provides novel fluorine-containing carboxylic acid compounds that are encompassed by following formula (II):

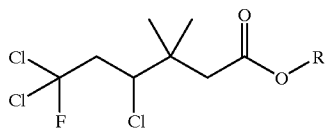

(II)

wherein R represents a lower alkyl (e.g., $C_{1-6}$ alkyl) or a hydrogen atom.

A method of producing said fluorine-containing carboxylic acid compounds of formula (II) comprises reacting a carboxylic acid compound encompassed by the following formula (III):

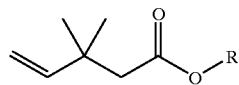

(III)

wherein R represents a lower alkyl (e.g., $C_{1-6}$ alkyl) group or a hydrogen atom, and trichlorofluoromethane in the presence of at least one metal salt, which is preferably selected from the group consisting of iron halides, copper halides, copper cyanides, and the like. Said carboxylic acid compounds of formula (II) which can be utilized in the methods of the instant invention are commercially available.

In addition, the methods of producing said fluorine-containing carboxylic acid compounds of formula (II) usually encompass reacting said carboxylic acid compound of formula (III) and trichlorofluoromethane together in the presence of one or more of the metal salts, under heated conditions and in an airtight container such as an autoclave. In this regard, said inventive fluorine-containing carboxylic acid compounds of formula (II) are preferably produced at the temperature of from about 40° C. to 300° C., and more preferably at the temperature of from about 90° C. to 180° C.

Said carboxylic acid compounds of formula (III) are typically utilized in the methods of the instant invention in an amount that is useful to produce said fluorine-containing carboxylic acid compounds of formula (II), but it is preferable for the method of the instant invention to utilize said carboxylic acid compounds of formula (III) in an amount wherein the molar ratio of said carboxylic acid compound of formula (III) to the trichlorofluoromethane is from about 0.1:1 mole to 10:1 moles. The methods of producing said fluorine-containing carboxylic acid compounds of formula (II) can be performed within or without a solvent, but it is thought to be preferable to produce said fluorine-containing carboxylic acid compounds of formula (II) in a solvent. Examples of the solvents which may be utilized in the method of producing said fluorine-containing carboxylic acid compounds of formula (II) include alcohols such as methanol, ethanol, isopropanol and t-butanol, hydrocarbons such as benzene and toluene, nitriles such as acetonitriles, and the like, or a combination thereof.

The metal salts utilized in the methods of producing said fluorine-containing carboxylic acid compounds of formula (II) are preferably selected from the group consisting of iron halides, copper halides, copper cyanides, and the like, or hydrates thereof, but are not explicitly limited thereto. Examples of the iron halides which may be utilized in the methods of producing said fluorine-containing carboxylic acids of formula (II) as the metal salts include ferrous salts such as iron (II) chloride and iron (II) bromide, ferric salts such as iron (III) chloride and iron (III) bromide, and the like. Examples of copper halides which may be utilized in the methods of producing said fluorine-containing carboxylic acid compounds of formula (II) as the metal salts include cuprous salts such as copper (I) chloride and copper (I) bromide, cupric salts such as copper (II) chloride and copper (II) bromide, and the like. Examples of the copper cyanides which may be utilized in the methods of producing said fluorine-containing carboxylic acid compounds of formula (II) as the metal salts include copper cyanide salts such as copper (I) cyanide, copper (II) cyanide, and the like.

To produce said fluorine-containing carboxylic acid compounds of formula (II), the metal salts may be utilized in an amount that effectively produces said fluorine-containing carboxylic acid compounds. Even if such is the case, it is preferable to utilize the metal salts in an amount wherein the molar ratio of the metal salts to said carboxylic acid compound of formula (III), which is utilized in the methods of producing said fluorine-containing carboxylic acid compounds of formula (II), is about from 0.001:1 to 1:1.

In addition, the methods of producing said fluorine-containing carboxylic acid compounds of formula (II) preferably comprise adding a reaction auxiliary. Examples of the reaction auxiliaries which may be utilized to produce the fluorine-containing carboxylic acid compounds of formula (II) include amines such as ethanolamines; pyridines; amine salts such as diethylamine hydrochloride; phosphoric acid esters such as triethyl phosphite; benzoin, and the like. The reaction auxiliaries should typically be utilized in the methods of producing said fluorine-containing carboxylic acid compounds of formula (II) in an amount that is useful in allowing a reaction to be performed without obstacles, and it is thought to be preferable to utilize the reaction auxiliary in an amount wherein the molar ratio of the reaction auxiliary to said carboxylic acid compound of formula (III) is from about 0.1:1 to 1:1 mole.

If so desired, the methods of producing said fluorine-containing carboxylic acid compounds of formula (II) may additionally comprise work-up operations subsequent to reacting the carboxylic acid compound of formula (III) and trichlorofluoromethane, as well as distilling a residue achieved from the work-up operations. The work-up operations are typically performed on the products of the reaction, with examples of the work-up operations including acid treatments, organic solvent extractions, concentrations, and the like, or a combination thereof. Thereafter, a residue achieved from such work-up operations may be distilled so that the leftover carboxylic acid compounds of formula (III) can be recovered at the fractions of distillates that boil at a low temperature and the fluorine-containing carboxylic acid compounds can be recovered at the fraction of distillates that boil at higher temperatures. Further, the recovered carboxylic acid compounds of formula (III) at the low boiling fraction of distillates can be reused as reaction components in the methods of the instant invention.

In this regard, 3-(2-chloro-2-fluorovinyl)-2,2-dimethylcyclopropane carboxylic acid compounds of formula (I) are usually produced according to the instant invention by reacting fluorine-containing carboxylic acid compounds of formula (II) and a base. In such cases, said 3-(2-chloro-2-fluorovinyl)-2,2-dimethylcyclopropane carboxylic acid compounds of formula (I) may be produced by utilizing the base in an amount of from about 2 or more moles per 1 mole of said fluorine-containing carboxylic acid compounds of formula (II), but it is preferable to utilize 2 to 4 moles of the base per 1 mole of said fluorine-containing carboxylic acid compounds. Examples of the base which may be utilized in the methods of producing 3-(2-chloro-2-fluorovinyl)-2,2-dimethylcyclopropane carboxylic acid compounds of formula (I) include alkali metal alkoxides such as sodium methylate, sodium ethylate, potassium-t-butoxide and sodium-t-pentoxide, alkali metal hydrides such as such as sodium hydride and potassium hydride, amines such as diazabicyclo-[5,4,0]-7-undecene (DBU) and piperidine, and the like.

In addition, the fluorine-containing carboxylic acid compounds of formula (II) and the base can be reacted together within or without a solvent, preferably in a solvent, to produce 3-(2-chloro-2-fluorovinyl)-2,2-dimethylcyclopropane carboxylic acid compounds of formula (I). Exemplarily of the solvents which may be used to produce said 3-(2-chloro-2-fluorovinyl)-2,2-dimethylcyclopropane carboxylic acid compounds include hydrocarbons such as toluene, ethers such as tetrahydrofuran, alcohols such as methanol and ethanol, dimethylformamide, and the like.

If such is the case, fluorine-containing carboxylic acid compounds of formula (II) can be utilized to produce said 3-(2-chloro-2-fluorovinyl)-2,2-dimethylcyclopropane carboxylic acid compounds of formula (I) by reacting the same and a base at a temperature of from about 20° C. to the boiling point of the solvent which is utilized therein. However, the 3-(2-chloro-2-fluorovinyl)-2,2-dimethylcyclopropane carboxylic acid compounds of formula (I) are preferably produced at a temperature of from about 20° C. to 120° C.

Furthermore, processes for preparing 3-(2-chloro-2-fluorovinyl)-2,2-dimethylcyclopropane carboxylic acid compounds of formula (I) may comprise work-up operations subsequent to the above noted reaction, if so desired. The work-up operations are typically performed on the products of said reaction, in order to enhance the recovery of 3-(2-chloro-2-fluorovinyl)-2,2-dimethylcyclopropane carboxylic acid compounds of formula (I). Examples of the work-up operations include acid treatments, organic solvent extractions, concentrations, and the like.

EXAMPLES

Hereinafter, the instant invention is further described by providing examples, but it is to be understood that the instant invention is not to be limited by these examples, since those of ordinary skill in the art will readily recognize that various changes can be made in the reactants, materials and procedures utilized in the examples, without departing from the spirit or scope of the instant invention.

Example 1

Five grams (5.00 g) of methyl 3,3-dimethyl4-pentenoate, 5.00 g of t-butanol, 1.08 g of ethanolamine, 350 mg of copper (I) chloride and 12.0 g of trichlorofluoromethane were added into a 50 mL bombenrohr. After sealing such achieved contents, the sealed contents were heated at 130° C. for 17 hours and at a pressure of 6 kg/cm$^2$ or lower. After allowing the contents to cool to room temperature, the contents were unsealed and poured into a liquid mixture comprising 30 mL of saturated ammonium aqueous chloride solution and 30 mL of t-butyl methyl ether. Subsequently, the achieved liquid mixture was stirred for 15 minutes, and the aqueous layer was extracted twice by using 30 mL of t-butyl methyl ether, so that the organic layers can be separated therefrom. The achieved organic layers are combined, washed thrice by using water, and further washed by using 30 mL of brine, in order to dry such over magnesium sulfate. After the magnesium sulfate was filtered out, the filtrate was concentrated, in order to obtain 7.49 g of a residue. The achieved residue was then subjected to reduced pressure distilling operations which utilized a distiller comprising a Vigreux column, to preliminarily obtain 2.37 g of methyl 3,3-dimethyl4-pentenoate (47%: boiling point; 52° C. (20 mm Hg) and then obtain 5.02 g of methyl 4,6,6-trichloro-6-fluoro-3,3-dimethylhexanoate (which is an inventive fluorine-containing carboxylic acid compound of formula (II)). The yield of 4,6,6-trichloro-6-fluoro-3,3-dimethylhexanoate was 97%, when considering the recovered rate of the contents of the later fraction of distillate. The boiling point of the recovered 4,6,6-trichloro-6-fluoro-3,3-dimethylhexanoate was 114 to 117° C. at 5 mmHg.

The following sets forth the results from analyzing the recovered 4,6,6-trichloro-6-fluoro-3,3-dimethylhexanoate by using NMR. $^1$H-NMR (CDCl$_3$, TMS internal standard) δ value (ppm): 1.12 (s, 3H), 1.19 (s, 3H), 2.32 (d, 1H), 2.62 (d, 1H), 2.92–3.06 (m, 2H), 3.69 (s, 3H), 4.43 (dd, 1H)

Example 2

A liquid mixture containing 398 mg of methyl 4,6,6-trichloro-6-fluoro-3,3-dimethylhexanoate and 1.10 g of a 28% solution of sodium methoxide/methanol was stirred at room temperature for 1 hour and was further stirred at the temperature of reflux for 6.5 hours. After allowing the liquid mixture to cool to room temperature, 10 mL of a saturated aqueous solution of ammonium chloride was added thereto, and the achieved liquid mixture was stirred for 15 minutes. Subsequently, the achieved liquid mixture had the aqueous layer extracted thrice by using 10 mL of hexane, and the achieved organic layer were then washed by using 10 mL of saturated brine, in order to dry the achieved organic layer over magnesium sulfate. After filtering the magnesium sulfate out of the achieved organic layer, the filtrate was concentrated to obtain a residue. The achieved residue was then subjected to thin layer chromatography, in which the eluent in the thin layer chromatography was a mixture which had a Rf value of 0.24 and that comprised 20 parts of hexane per 1 part of ethyl acetate. As such, 224 mg of methyl 3-(2-chloro-2-fluorovinyl)-2,2-dimethylcyclopropanecarboxylate was recovered, with a yield of 76%.

The recovered methyl 3-(2-chloro-2-fluorovinyl)-2,2-dimethylcyclopropanecarboxylate was then analyzed by NMR to detect a trans-(E) isomer thereof, trans-(Z) isomer thereof, cis-(E) isomer thereof, and cis-(Z) isomer thereof, at a ratio of 45:45:5:5. As used herein, the "trans" and "cis" represent the stereoisomers relating to the substituent groups at the 1 and 3 positions of the cyclopropane ring of 3-(2-chloro-2-fluorovinyl)-2,2-dimethylcyclopropanecarboxylate; and the (E) and (Z) represent the geometric isomers relating to the vinyl group of 3-(2-chloro-2-fluorovinyl)-2,2-dimethylcyclopropanecarboxylate.

The following sets forth the results from analyzing the recovered 3-(2-chloro-2-fluorovinyl)-2,2-dimethylcyclopropanecarboxylate by NMR. $^1$H-NMR (CDCl$_3$, TMS internal standards) δ value (ppm) trans-(E) isomer: 1.17 (s, 3H), 1.26 (s, 3H), 1.53 (d, 1H), 2.17–2.24 (m, 2H), 3.69 (s, 3H), 4.66 (dd, 1H) trans-(Z) isomer: 1.16 (s, 3H), 1.28 (s, 3H), 1.51 (d, 1H), 2.02 (dd, 1H), 3.70 (s, 3H), 5.10(dd, 1H) cis-(E) isomer: 1.23 (s, 3H), 1.24 (s, 3H), 1.79 (d, 1H), 2.05 (dt, 1H), 3.66 (m, 3H), 5.34 (dd, 1H) cis-(Z) isomer: 1.22 (s, 3H), 1.24 (s, 3H), 1.77 (d, 1H), 1.81 (dt, 1 H), 3.66 (s, 3H), 5.74 (dd, 1H)

The above Examples result evidence that surprising and advantageous properties are possessed by the instant invention, when a fluorine-containing carboxylic acid compound of formula (II) which is provided by the instant invention, participates in a reaction with a base, in order to produce 3-(2-chloro-2-fluorovinyl)-2,2-dimethyl cyclopropanecarboxylic acid compounds of formula (I).

What is claimed is:

1. A fluorine-containing carboxylic acid or ester compound of formula (II):

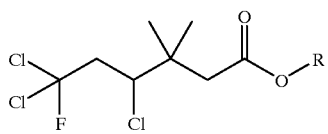

(II)

wherein R represents a $C_{1-6}$ alkyl group or a hydrogen atom.

2. A method of producing a 3-(2-chloro-2-fluorovinyl)-2,2-dimethyl cyclopropanecarboxylic acid or ester compound of formula (I):

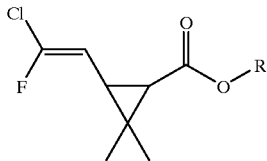

(I)

wherein R represents a $C_{1-6}$ alkyl group or a hydrogen atom, comprising:

reacting together a fluorine-containing carboxylic acid or ester compound of formula (II):

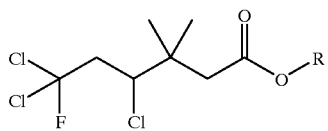

(II)

wherein R represents a $C_{1-6}$ alkyl group or a hydrogen atom, and a base.

3. The method according to claim 2, wherein said fluorine-containing carboxylic acid or ester compound of formula (II) is produced by a process comprising:

reacting together a carboxylic acid or ester compound of formula (III):

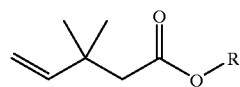

(III)

wherein R represents a $C_{1-6}$ alkyl group or a hydrogen atom, and trichlorofluoromethane in the presence of at least one metal salt.

4. The method according to claim 3, wherein said at least one metal salt is selected from the group consisting of an iron halide, a copper halide, a copper cyanide, and hydrates thereof.

5. The method according to claim 4, wherein said carboxylic acid or ester compound of formula (III) and said trichlorofluoromethane are reacted together at a temperature of from 40° C. to 300° C.

6. The method according to claim 4, wherein a molar ratio of said carboxylic acid or esther compound of formula (III) to said trichlorofluoromethane is from 1:0.1 to 1:10.

7. The method according to claim 4, wherein a molar ratio of said at least one metal salt to said carboxylic acid or ester compound of formula (III) is from 0.001:1 to 1:1.

8. The method according to claim 5, wherein a molar ratio of said carboxylic acid or ester compound of formula (III) to said trichlorofluoromethane is from 1:0.1 to 1:10.

9. The method according to claim 5, wherein a molar ratio of said at least one metal salt to said carboxylic acid or ester compound is from 0.001:1 to 1:1.

10. The method according to claim 8, wherein a molar ratio of said at least one metal salt to said carboxylic acid or ester compound is from 0.001:1 to 1:1.

11. A method of producing a fluorine-containing carboxylic acid or ester compound of formula (II):

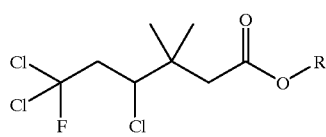

(II)

wherein R represents a $C_{1-6}$ alkyl group or a hydrogen atom, said method comprising:

reacting together a carboxylic acid or ester compound of formula (III):

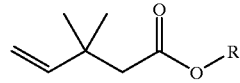

(III)

wherein R represents a $C_{1-6}$ alkyl group or a hydrogen atom, and trichlorofluoromethane in the presence of at least one metal salt.

12. The method according to claim 11, wherein said at least one metal salt is selected from the group consisting of an iron halide, a copper halide, a copper cyanide, and hydrates thereof.

* * * * *